United States Patent
Cook et al.

(10) Patent No.: US 8,145,019 B1
(45) Date of Patent: Mar. 27, 2012

(54) SELF ADAPTING SENSOR

(75) Inventors: Gary Cook, Beavercreek, OH (US); Dean R. Evans, Beavercreek, OH (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 383 days.

(21) Appl. No.: 12/483,880

(22) Filed: Jun. 12, 2009

Related U.S. Application Data

(60) Provisional application No. 61/132,342, filed on Jun. 12, 2008.

(51) Int. Cl.
*G02B 6/34* (2006.01)
(52) U.S. Cl. .......................................... 385/37
(58) Field of Classification Search ........................ None
See application file for complete search history.

(56) References Cited

U.S. PATENT DOCUMENTS 4,474,427 A * 10/1984 Hill et al. ...................... 385/123

OTHER PUBLICATIONS

K.O. Hill et al. Photosensitivity in optical fiber waveguides: Application to reflection filter fabrication. Applied Physics Letters 32:10:647-649, May 1978.*
P. Mills et al. Holographically formed, highly selective, infra-red filter in iron-doped lithium niobate. Electronics Letters 21:20:885-886, Sep. 1985.*
Stratophase, "Technology Overview", taken from www.stratophase.com, Jun. 10, 2009.

* cited by examiner

*Primary Examiner* — Mike Stahl
(74) *Attorney, Agent, or Firm* — AFMCLO/JAZ; Charles Figer

(57) ABSTRACT

The present invention provides a method for adjusting a diffraction grating to changes in ambient conditions. The method includes writing a diffraction grating in the photorefractive waveguide with a laser, measuring spectral characteristics of the diffraction grating, and allowing the diffraction grating to self-write from interference between a forward beam and a Fresnel reflection, such that the diffraction grating is adjusted for changes in ambient conditions.

10 Claims, No Drawings

SELF ADAPTING SENSOR

CROSS-REFERENCE TO RELATED APPLICATION

The present application relates to and claims priority to U.S. Provisional Patent Application No. 61/132,342 filed Jun. 12, 2008. The contents of U.S. Provisional Patent Application No. 61/132,342 are hereby incorporated by reference.

RIGHTS OF THE GOVERNMENT

The invention described herein may be manufactured and used by or for the Government of the United States for all governmental purposes without the payment of any royalty.

FIELD OF THE INVENTION

The present invention relates to the use of photorefractive materials as self-writing surface waveguide optical sensors that are insensitive to changes in the ambient conditions.

BACKGROUND OF THE INVENTION

Photorefractives are able to create real-time holograms through the interference of two or more laser beams within the photorefractive material. The hologram can take the form of a real or virtual image of an object or data, or, in the simplest case, form a diffraction grating. Generally, a diffraction grating is an optical component with a regular pattern, which splits and diffracts light into several beams travelling in different directions. The diffraction grating can be either in phase with the optical interference pattern or out of phase. When in phase, the diffraction grating behaves in the same way as any common diffraction grating, causing equal diffraction of each of the writing beams. However, if the diffraction grating is out of phase with respect to the optical interference pattern, power may be transferred from one or more beams to another. This well established technique is useful for amplifying weak signal beams and for coherently combining two or more beams into a single stronger laser beam.

Diffraction gratings within waveguide structures have previously been used as extremely sensitive optical sensors. The method relies on placing a diffraction grating (a Bragg grating) within a thin optical waveguide at the surface of a transparent substrate. The electric field component of the guided light is able to penetrate a very small distance beyond the confines of the waveguide surface into the surrounding environment. This surface electric field is often called the evanescent field. The propagation of the light within the surface waveguide is highly sensitive to any changes of the surface refractive index, even changes which occur within the evanescent field above the surface. The reflectivity and wavelength selectivity of the surface waveguide diffraction grating are therefore sensitive to any changes of the evanescent field. Materials which come into contact with (or very close to) the surface influence the effective surface refractive index and can be detected by monitoring changes in the optical properties of the embedded diffraction grating. Optical fibers and surface waveguides have both been used successfully for this application and the best devices are capable of detecting fifth decimal place changes in refractive index. Typical applications include biological sensors, refractive index measurement, and product and substance identification.

SUMMARY OF THE INVENTION

The present invention provides a method for self-writing a diffraction grating for sensitive optical detection of biological, chemical and optical materials; self-adapting Bragg gratings to eliminate the influence of changes in ambient conditions such as temperature and humidity; and flexible "lab on a chip" analysis using simple detection methods.

In accordance with one aspect of the invention, there is provided a method for adjusting a diffraction grating to changes in ambient conditions. The method includes providing a photorefractive waveguide, writing a diffraction grating in the photorefractive waveguide with a laser, measuring spectral characteristics of the diffraction grating, and allowing the diffraction grating to self-write from interference between a forward beam and a Fresnel reflection, such that the diffraction grating is adjusted for changes in ambient conditions. The changes in ambient conditions may include changes in temperature, humidity, and/or the presence of biological, chemical, or optical material.

The method may also include introducing a substance into proximity with a surface of the photorefractive waveguide, and turning off the laser prior to introducing the substance. The substance may be, or may represent, a biological or chemical material, dust, moisture, or any other airborne particulate.

The photorefractive waveguide includes a photorefractive material such as, for example, iron doped lithium niobate and/or a photorefractive polymer. The photorefractive waveguide may be planar or channel.

DETAILED DESCRIPTION OF THE INVENTION

Although surface waveguide Bragg gratings are capable of extreme sensitivity, fixed Bragg gratings are prone to changes in ambient conditions such as temperature and humidity fluctuations. For optimum sensitivity, the ambient conditions must be carefully controlled. However, if the waveguide Bragg grating is photorefractive in nature, the grating can be written "real-time", so that the diffraction grating adapts to changes in the ambient conditions. Detection is effected by first writing the grating in the photorefractive waveguide and then monitoring the spectral characteristics of the grating as unknown substances are brought into close proximity with the surface. Preferably, the laser should either be switched off immediately prior to the measurements, or the photorefractive response time should be much longer than the measurement time. Either of these options will ensure that the Bragg grating will not self-adapt to accommodate the sensed material. The advantage of this method is that the Bragg grating can be written by any convenient laser source and will self-write from interference between the forward beam and the Fresnel reflection from the waveguide exit. Power transfer between these two beams makes the technique more sensitive than simple Bragg diffraction.

One exemplary material for this application is iron doped lithium niobate (Fe:LiNbO$_3$). The material is low cost, has a very high optical quality, and will remain photorefractive over the entire Mil. Spec. temperature range. Fe:LiNbO$_3$ is also an ideal material for forming surface optical waveguides using a variety of methods such as metal (e.g. titanium) indiffusion, proton exchange, ion implantation, epitaxial deposition, surface stoichiometry modifications, and mechanical layering. The techniques of proton exchange or metal indiffusion are the most preferred for the creation of surface waveguides in Fe:LiNbO$_3$, being low cost and suitable for mass-production. The waveguides may be either planar or channel in nature, depending on the eventual sensor requirements. Laser coupling into and out of the waveguide structure may be effected by the use of surface coupling methods (e.g. prisms), or by end-coupling directly to free-space or fiber optics. The latter has the advantage of being a robust method but requires greater assembly precision. The waveguide may either be configured as a single sensor, or may be optically coupled (e.g. interferometrically) to parallel or serial additional waveguides for differential detection methods with improved sensitivity and selectivity of detection.

In all cases, the Bragg grating is self-written immediately prior to detection by passing a coherent laser light into the waveguide. Interference between the input light and the Fresnel reflection of this light from the waveguide exit will automatically generate a photorefractive Bragg reflection grating within the waveguide. It is also possible to arrange for several different laser wavelengths to simultaneously or sequentially write superimposed Bragg gratings of different spacings within single or multiple guides for hyperspectral detection.

Although one method of writing Bragg gratings is described above, it is also possible to achieve similar results using an external laser source to write gratings with periods longer than those created by self-pumped reflection gratings as described above. Two angularly separated laser beams intersecting the surface may write a grating with a coarse period. The Bragg matched grating wavelength within the guide may then be at a wavelength considerably longer than the writing laser wavelengths. This allows infra-red lasers to be used for detection while visible lasers would be used for writing the grating. Likewise, ultra-violet lasers could be used in the same way to write a grating that is probed using a visible laser. The ultra-violet writing can also be used with undoped lithium niobate, using inter-band absorption to generate the necessary photorefractivity. Using different wavelength lasers for writing and detection may have advantages in reducing detection noise from scattered light.

In addition to photorefractive surface waveguides, the present invention may also be effected using bare, or partially clad, photorefractive fibers. The fibers may either be used free-standing, or they may be bonded to a supporting substrate. Fibers of Fe:LiNbO$_3$ have been produced by a variety of methods, including laser heated pedestal growth.

Although the present invention is described in terms of lithium niobate, in principle, any photorefractive material can be used, including photorefractive polymers.

While various descriptions of the present invention are described above, it should be understood that the various features can be used singly or in any combination thereof.

Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for adjusting a diffraction grating in a photorefractive waveguide in response to changes in ambient conditions, the method comprising:
    writing an initial diffraction grating in the photorefractive waveguide with a laser;
    passing a coherent laser light into the photorefractive waveguide;
    interfering the coherent laser light and a Fresnel reflection of the coherent laser light to generate a new photorefractive reflection grating within the waveguide; and
    writing in real-time the new photorefractive grating to adjust for the changes in ambient conditions.

2. The method of claim 1 wherein changes in ambient conditions includes changes in temperature.

3. The method of claim 1 wherein changes in ambient conditions includes changes in humidity.

4. The method of claim 1 wherein changes in ambient conditions includes the presence of biological or chemical materials.

5. The method of claim 1 further comprising the step of introducing a substance into proximity with a surface of the photorefractive waveguide.

6. The method of claim 5 further comprising the step of turning off the laser prior to introducing the substance.

7. The method of claim 1 wherein the photorefractive waveguide includes iron doped lithium niobate.

8. The method of claim 1 wherein the photorefractive waveguide includes a photorefractive polymer.

9. The method of claim 1 wherein the photorefractive waveguide is planar.

10. The method of claim 1 wherein the photorefractive waveguide is channel.

* * * * *